United States Patent
Gydesen et al.

[11] Patent Number: 6,041,805
[45] Date of Patent: Mar. 28, 2000

[54] VALVE ASSEMBLY FOR A REMOVABLE INK CARTRIDGE

[75] Inventors: H. Chris Gydesen, Oakdale; Russell A. Roiko, Rogers; James E. Zenk, St. Paul, all of Minn.; Kay F. Schilli, Portland, Oreg.

[73] Assignee: Imation Corp., Oakdale, Minn.

[21] Appl. No.: 09/110,991

[22] Filed: Jul. 7, 1998

[51] Int. Cl.[7] .................................................. F16L 55/18
[52] U.S. Cl. .................. 137/15; 137/614.03; 137/614.04
[58] Field of Search ............................... 137/614, 614.04, 137/614.03, 614.02, 614.05, 150; 251/149.6, 149.3, 149.1, 149.7, 149.9; 355/256; 346/75

[56] References Cited

U.S. PATENT DOCUMENTS

| | | | |
|---|---|---|---|
| 2,485,006 | 10/1949 | Main, Jr. et al. | 137/614.03 |
| 2,765,181 | 10/1956 | Butterfield | 137/614.03 |
| 2,958,544 | 11/1960 | Wurzburger et al. | 137/614.03 |
| 3,417,781 | 12/1968 | Gregg | 137/614.04 |
| 3,645,294 | 2/1972 | Allread | 137/614.03 |
| 4,483,368 | 11/1984 | Panthofer | 137/614.04 |
| 4,597,413 | 7/1986 | Buseth | 137/614.04 |
| 4,639,738 | 1/1987 | Young et al. | 346/75 |
| 4,949,745 | 8/1990 | McKeon | 137/614.03 |
| 5,168,897 | 12/1992 | Vanderjagt | 137/614.02 |
| 5,211,197 | 5/1993 | Marrison et al. | 137/614.04 |
| 5,215,122 | 6/1993 | Rogers et al. | 137/614.04 |
| 5,293,913 | 3/1994 | Preszler | 141/367 |
| 5,365,973 | 11/1994 | Fink, Jr. et al. | 137/614.04 |
| 5,396,316 | 3/1995 | Smith | 355/256 |
| 5,402,826 | 4/1995 | Molnar et al. | 137/614.01 |
| 5,406,980 | 4/1995 | Allread et al. | 137/614.03 |
| 5,435,461 | 7/1995 | Smith et al. | 222/45 |
| 5,461,466 | 10/1995 | Girard et al. | 355/256 |
| 5,539,503 | 7/1996 | Johnson | 355/256 |
| 5,546,984 | 8/1996 | Arcaro | 137/614.03 |
| 5,650,253 | 7/1997 | Baker et al. | 430/119 |
| 5,652,282 | 7/1997 | Baker et al. | 523/201 |
| 5,655,194 | 8/1997 | Landa et al. | 399/238 |
| 5,709,243 | 1/1998 | Wells et al. | 137/614.03 |
| 5,828,395 | 10/1998 | Takata | 347/86 |
| 5,912,687 | 6/1999 | Cowger et al. | 251/353 |

FOREIGN PATENT DOCUMENTS

| | | |
|---|---|---|
| 0 687 846 | 12/1995 | European Pat. Off. . |
| 678 556 | 3/1952 | United Kingdom . |
| WO 96 21120 | 11/1996 | WIPO . |

*Primary Examiner*—Denise L. Ferensic
*Assistant Examiner*—Joanne Y. Kim
*Attorney, Agent, or Firm*—William D. Bauer

[57] ABSTRACT

A method and valve assembly for fluidly coupling a removable ink cartridge to an imaging device. The valve assembly includes a first assembly portion and a second assembly portion. The first assembly portion includes a first housing having a first valve portion biased to a closed position. The first valve portion has a first interface surface at a distal end. A second assembly portion includes a second housing having a second valve portion biased to a closed position. The second valve portion has a second interface surface at a distal end adapted to engage with the first interface surface at a valve interface. A forward seal adapted to engage with the first interface surface and the second interface surface is positioned at the valve interface when the first and second valve portions are in the closed position.

22 Claims, 4 Drawing Sheets

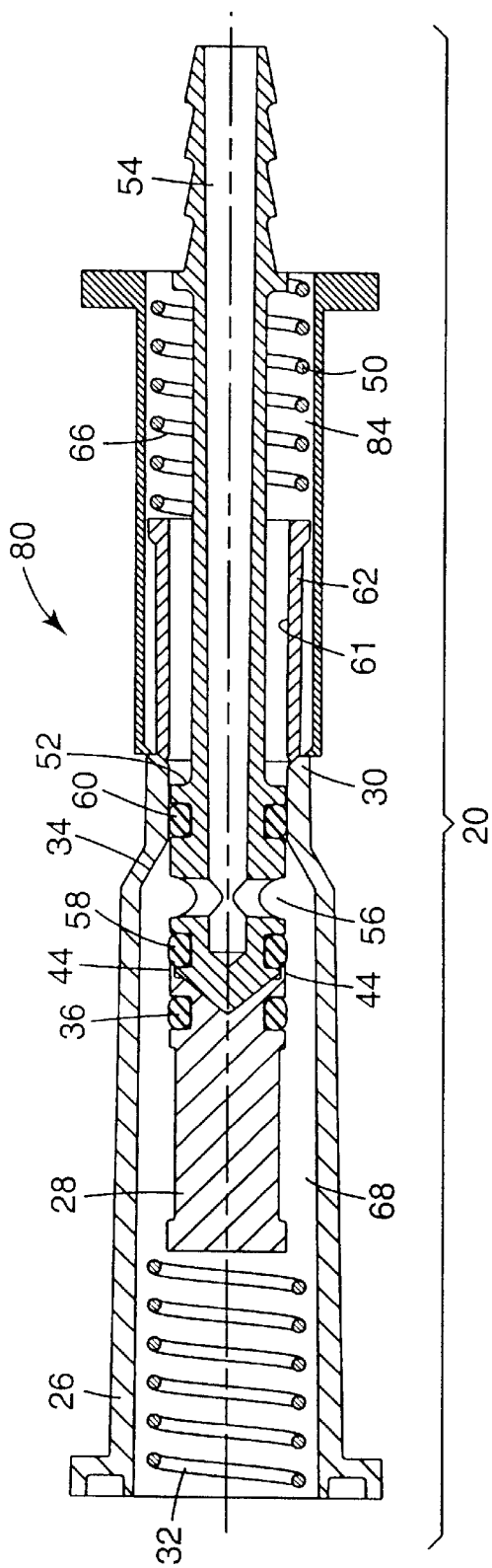
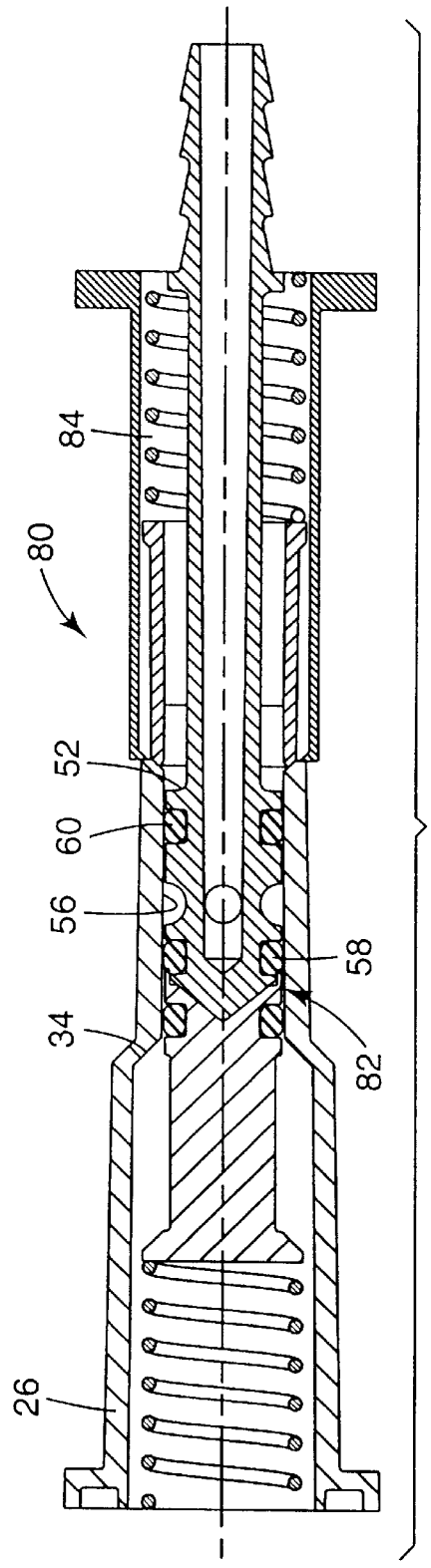
Fig. 3
Fig. 4

VALVE ASSEMBLY FOR A REMOVABLE INK CARTRIDGE

FIELD OF THE INVENTION

The present invention relates to a valve assembly for fluidly coupling a user replaceable ink cartridge to an electrographic imaging device and to an ink cartridge utilizing the present valve assembly.

BACKGROUND OF THE INVENTION

Removable/refillable ink cartridges are commonly used for supplying liquid ink to electrographic imaging devices. Some electrographic imaging devices may maintain a positive pressure of liquid ink, carrier and/or printed down ink at the cartridge interface even when the cartridge is removed. To accommodate such replaceable ink cartridges, an interconnect must be provided that enables the cartridge to be easily and reliably replaced, while preventing liquid ink from leaking from the imaging device or the cartridge. One source of leakage is the physical interface of the interconnect.

U.S. Pat. No. 5,546,984 (Arcaro) discloses a bellows type, low spillage, quick disconnect unit for an electrophotographic printer. A bellows concentrically surrounds a plunger and extends from an inlet housing to an expanded tip of the plunger. The bellows has an engagement end that rubs against the expanded tip, thereby sealing the interior of bellows from the external environment. No seals are disclosed to prevent fluid from collecting on the expanded tip.

U.S. Pat. No. 5,461,466 (Girard et al.) discloses a dripless seal for a liquid toner cartridge that utilizes a foam material to absorb any excess fluid that remains on the external face of the fluid coupling. Again, no seals are disclosed to prevent fluid from collecting at the valve interface.

Therefore, what is required is an improved, self-sealing valve assembly that minimizes dripping and leakage during multiple engagement and disengagement cycles of a removable ink cartridge to an imaging device.

SUMMARY OF THE INVENTION

The present invention relates to a method and valve assembly for fluidly coupling a removable ink cartridge to an imaging device. The valve assembly is a conduit for transporting imaging fluids between the ink cartridge and the electrographic imaging device. The present invention is also directed to an ink cartridge utilizing a portion of the present valve. The present self-sealing valve assembly minimizes dripping and leakage during multiple engagement and disengagement cycles of a removable ink cartridge to an imaging device.

In one embodiment, the valve assembly includes a first assembly portion and a second assembly portion. The first assembly portion includes a first housing having a first valve portion biased to a closed position. The first valve portion has a first interface surface at a distal end. A second assembly portion includes a second housing having a second valve portion biased to a closed position. The second valve portion has a second interface surface at a distal end adapted to engage with the first interface surface at a valve interface. A forward seal adapted to engage with the first interface surface and the second interface surface is positioned at the valve interface when the first and second valve portions are in the closed position.

In one embodiment, the forward seal is located on the second valve portion. The forward seal is engaged with the first interface surface and the second interface surface at the valve interface when the first and second valve portions are in an open position. The forward seal is engaged with the first interface surface and the second interface surface at the valve interface until disengagement of the first and second valve portions. The valve interface is preferably a fluid tight seal. The fluid tight seal is maintained when the first and second valve portions are in an open position.

In one embodiment, a raised portion extends around a perimeter of the first interface surface adapted to engage with the forward seal. In another embodiment, the first interface surface has a shape generally complementary to a shape of the second interface surface. In yet another embodiment, the first interface surface is self-centering when engaged with the second interface surface. The first and second interface surfaces can be generally conical or a variety of other shapes.

In an alternate embodiment, at least one of the interface surfaces is an elastomeric material. The forward seal can be integrally formed with one of the valve portions. In another embodiment, at least one of the valve portions is an elastomeric material.

In one embodiment, the forward seal is located on a distal end of the second valve portion. A fluid channel is located on the second valve portion behind the forward seal. A rear seal is located behind the fluid channel. A sleeve is biased to engage with the forward seal and the rear seal when the second assembly portion is in the closed position. The first housing biases the sleeve into the second housing when the valve assembly is in an engaged configuration.

The present invention is also directed to an ink cartridge for an electrographic imaging device. The electrographic imaging device has a first valve portion with a first interface surface at a distal end. The ink cartridge includes a second assembly portion comprising a second housing having a second valve portion biased to a closed position. The second valve portion has a second interface surface at a distal end adapted for self-centering engagement with the first interface surface at a valve interface. A forward seal is adapted to engage with the first interface surface and the second interface surface at the valve interface when the first and second valve portions are in the closed position.

The present invention is also directed to a method of fluidly coupling a removable ink cartridge to an imaging device, comprising the steps of biasing a first valve portion of a first assembly portion in a valve assembly to a closed position, the first valve portion having a first interface surface at a distal end; biasing a second valve portion of a second assembly portion in the valve assembly to a closed position, the second valve portion having a second interface surface at a distal end adapted to engage with the first interface surface at a valve interface; positioning a forward seal adapted to engage with the first interface surface and the second interface surface at the valve interface when the first and second valve portions are in the closed position; advancing the first and second valve portions to an open position while maintaining the valve interface in a substantially fluid tight configuration; and disengaging the valve assembly while maintaining the valve interface in a substantially fluid tight configuration.

As used herein:

"electrographic" refers to electrostatic, electrophotographic and ionographic.

"imaging fluid" refers to liquid carrier, ink solids, liquid ink, ink concentrate, printed down ink, and working solution.

"ink concentrate" refers to ink at a concentration greater than the working solution concentration.

"imaging device" refers to printers, copiers, fax machines, and other image duplication systems.

"ink solids" refers to film-forming solids or film-forming toner particles.

"liquid carrier" refers to a solvent or other liquid into which the film-forming solids or film-forming toner particles are dispersed.

"liquid ink" refers to ink solids dispersed in a liquid carrier.

"printed down ink" or "depleted ink" refers to ink at a concentration of ink solids below the working solution concentration.

"working solution" refers to ink at about the working solution concentration.

"working solution concentration" refers to a concentration of ink solids suitable for developing a latent image on a receptor material in an electrographic imaging device.

BRIEF DESCRIPTION OF THE SEVERAL VIEWS OF THE DRAWING

FIG. 3 is a side sectional view of the valve assembly of FIG. 1 in an engaged configuration.

FIG. 4 is a top sectional view of the valve assembly of FIG. 3.

DETAILED DESCRIPTION OF THE INVENTION

Figure 1:
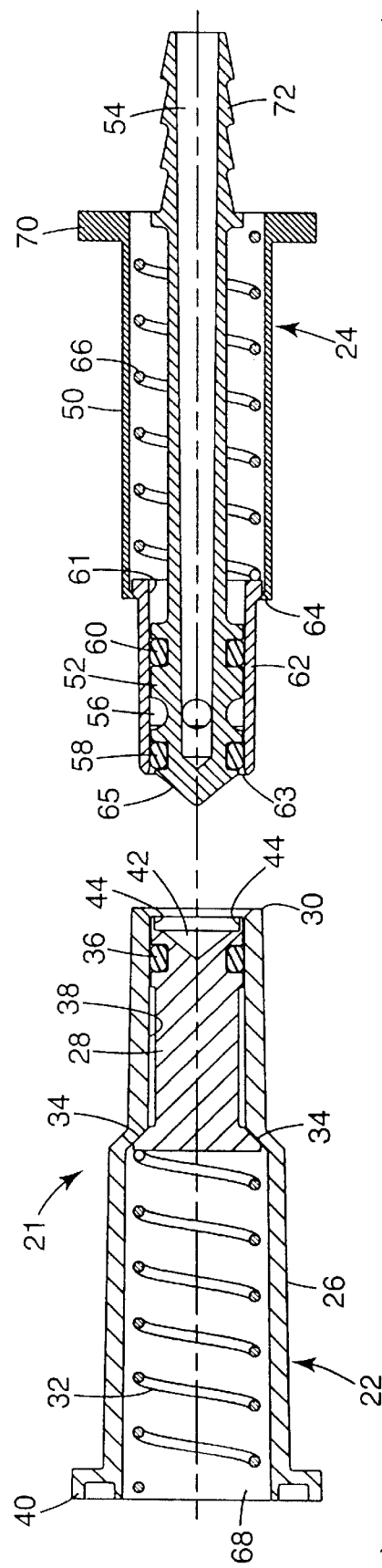
FIG. 1 is a side sectional view of a valve assembly in accordance with the present invention in a disengaged configuration.
Figure 2:
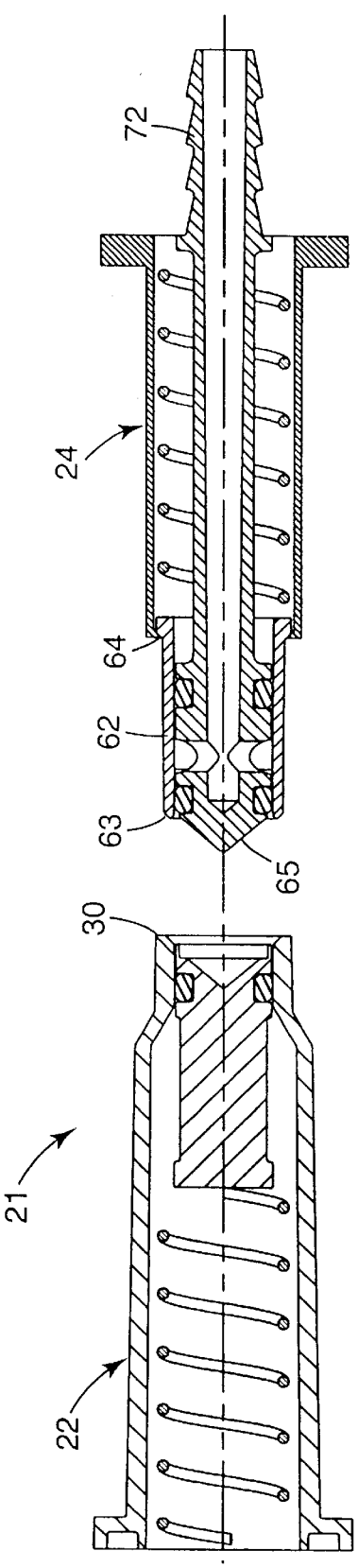
FIG. 2 is a top sectional view of the valve assembly of FIG. 1.

FIGS. 1 and 2 are sectional views of a valve assembly 20 in accordance with the present invention in a disengaged configuration 21. The valve assembly 20 includes a first assembly portion 22 and a second assembly portion 24. The first assembly portion 22 includes a first housing 26 containing a first valve portion 28. The first valve portion 28 is biased against hard stop 34 on the first housing 26 by spring 32. The first valve portion includes a seal 36 which rides along an internal bore 38 on the first housing 26. The first housing 26 includes a flange 40 for mounting to either a removable ink cartridge 400 or an imaging device 481 (see FIG. 6). Alternatively, the first housing 26 may be integrally formed with a portion of the ink cartridge 400 or imaging device 481.

The first valve portion 28 includes a first interface surface 42 in front of the seal 36. As used herein, the front of the first assembly portion 22 is located near the first interface surface 42 and the rear is located near the flange 40. In the illustrated embodiment, the first interface surface 42 has a generally conical shape, although a variety of other shapes may be used. Raised portion 44 is located around a perimeter of the first interface surface 42 adjacent to distal end 30 of the first housing 26 (see also FIG. 5).

The second assembly portion 24 includes a second housing 50 surrounding a second valve portion 52. In the illustrated embodiment, the second valve portion 52 includes second interface surface 65 having a shape generally complementary to the first interface surface 42. The relative shapes of the first and second interface surfaces 42, 65 preferably facilitate centering of the first valve portion 28 with the second valve portion 52. In the illustrated embodiment, the conical shaped protrusion of the second interface surface 65 is self-centering when engaged with the conical shaped recess of the first interface surface 42. The self-centering nature of the first and second valve portions 28, 52 permits the valve assembly 20 to be engaged and disengaged multiple times, with minimal or no leakage. Alternatively, the second housing 50 may be integrally formed with a portion of the ink cartridge 400 or imaging device 481.

The second valve portion 52 also includes a connector 72 for engagement with fluid handling equipment within the imaging device (see FIG. 6) and a flange 70 for mounting to an ink cartridge or imaging device. In the illustrated embodiment, the spatial relationship of the second housing 50 is fixed with respect to the second valve portion 52.

Second passageway 54 is fluidly coupled to a fluid channel 56. The fluid channel 56 is located between a forward seal 58 and a rear seal 60. A sleeve 62 surrounds the second valve portion 52. An internal bore 61 on the sleeve 62 forms a sealing engagement with the forward seal 58 and the rear seal 60. The sleeve 62 is biased by spring 66 against hard stop 64 on the second housing 50.

In the embodiment illustrated in FIG. 1 and 2, the first and second valve portions 28, 52 are in a closed position. As used here, the closed position refers to a configuration that prevents the flow of fluids through the valve assembly 20. The engagement of the forward seal 58 and the rear seal 60 with the sleeve 62 retains any fluid within the fluid channel 56 or second passageway 54. Similarly, the engagement of the seal 36 with the internal bore 38 on the first housing 26 retains any fluid in first passageway 68.

The forward seal 58 is preferably located adjacent to distal end 63 of the sleeve 62 for engagement with the raised portion 44. Consequently, a valve interface 82 (see FIGS. 3–5) is formed immediately upon engagement of the first and second assembly portions 22, 24, before the first or second valve portions 28, 52 are substantially displaced. The valve interface 82 is preferably fluid tight. That is, a substantially fluid tight seal is formed at the valve interface 82 during the initial phases of engagement of the first and second assembly portions 22, 24.

Various components of the valve assembly may be constructed from a variety of polymeric materials, such as acrylonitrile butadiene styrene resin (ABS), acetal, polyethylene, polypropylene, butyl rubber, or polycarbonate. The seals 36, 58, 60 may be constructed from a variety of elastomeric materials, such as silicone, silicone-type materials or butyl rubber. Elastomeric materials are polymeric materials, such as fluoroelastomers, synthetic rubbers or plastic, that at room temperature can be stretched under low stress to at least twice its original length and, upon immediate release of the stress, will return with force to its approximate original length. In one embodiment, one or more of the seals 36, 58, 60 are molded onto, or integrally with, the respective first and second valve portions 28, 52. In another embodiment, one or both of the first and second valve portions 28, 52 may be constructed from an elastomeric material. In this embodiment, the forward seal 58 is either unnecessary or is integral with the valve portions 28, 52.

Figure 5:
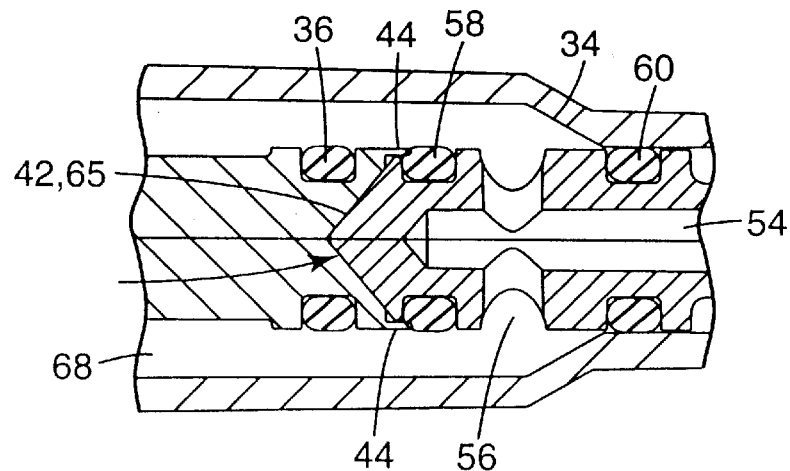
FIG. 5 is an enlarged view of the valve interface shown in FIG. 3.

FIGS. 3 through 5 illustrate the valve assembly 20 of FIGS. 1 and 2 in an engaged configuration 80. The raised portion 44 extending from the perimeter of the first interface surface 42 engages with the forward seal 58 on the second valve portion 52 at a valve interface 82 before either half of the valve assembly 20 is in the open position. Fluid flowing through the first passageway 68 does not collect at the valve interface 82. Consequently, when the valve assembly 20 is disengaged, fluid is typically not released and the interface surfaces 42, 65 are relatively free of imaging fluids.

In the embodiment illustrated in FIGS. 3 through 5, the distal end 30 of the first housing 26 pushes the sleeve 62 into the second housing 50, thereby fluidly coupling the fluid channel 56 with the first passageway 68. During the engagement process, the forward seal 58 and rear seal 60 wipe liquid from the internal bore 61 of the sleeve 62. Generally simultaneously, the second valve portion 52 pushes the first valve portion 28 into the first housing 26, thereby fluidly coupling the fluid channel 56 with the first passageway 68. In the embodiment illustrated in FIGS. 3 and 4, the valve assembly 20 is fully engaged and in a fluidly coupled relationship. Fluid can now travel between the second passageway 54 and the first passageway 68. Fluid can also travel in the reverse direction.

When the valve assembly 20 is disengaged, the spring 32 pushes the first valve portion 28 until it hits hard stop 34. Simultaneously, the spring 66 pushes the sleeve 62 over the rear seal 60, the fluid channel 56, and finally the forward seal 58. During the disengagement process, the forward seal 58 and the rear seal 60 first wipe any liquid from the internal bores 38 on the first housing 26. Subsequently, the seals 38, 60 wipe any liquid from the internal bore 61 of the sleeve 62 and deposit it in chamber 84.

Figure 6:
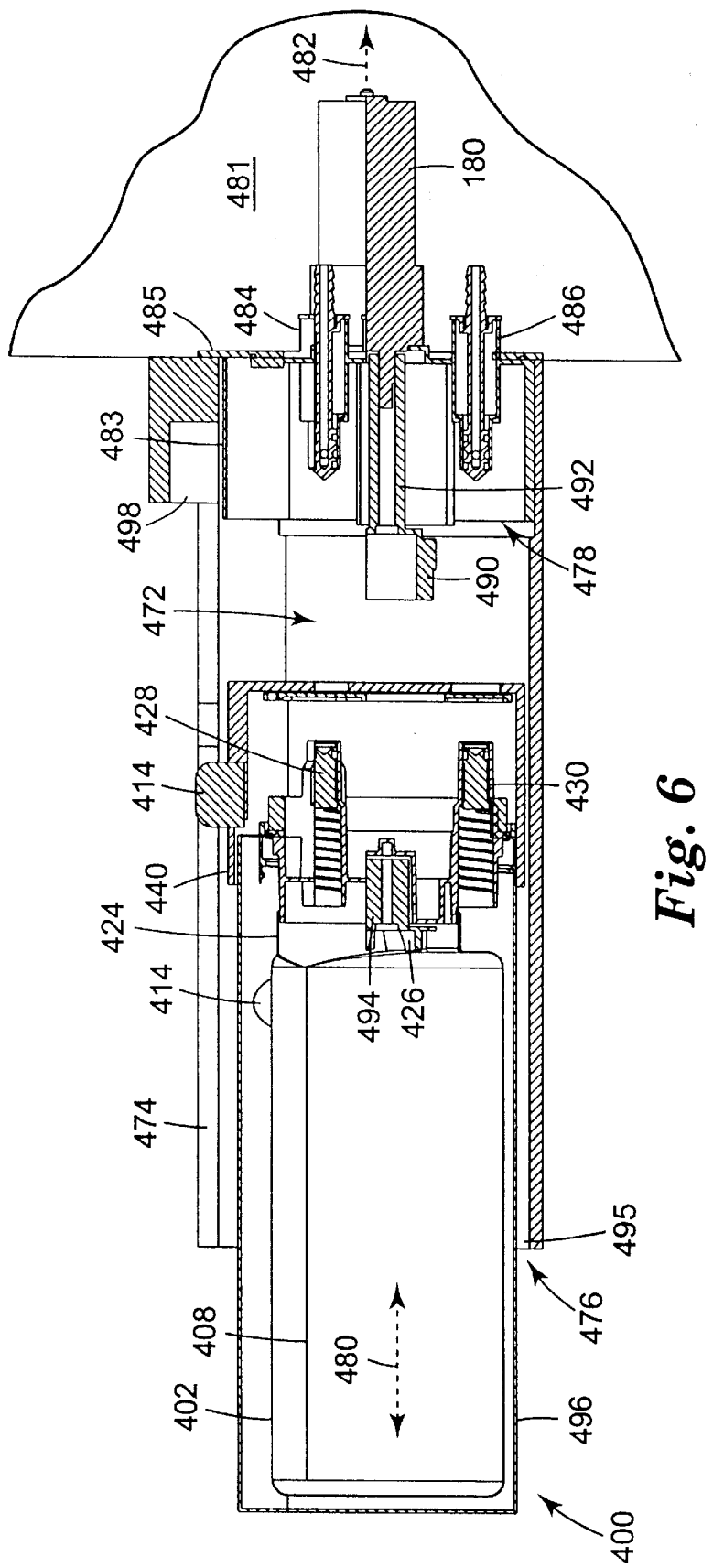
FIG. 6 is a side sectional view of an ink cartridge and cartridge assembly interface utilizing a valve assembly in accordance with the present invention.

FIG. 6 is a cross-sectional side view of a multi-compartment ink cartridge 400 partially inserted into an ink cartridge bay 472 of a imaging device housing 474. Other embodiments of the ink cartridge 400 are disclosed in commonly assigned patent application entitled Ink Cartridge for a Liquid Electrographic Imaging Device, (Attorney docket No. 53744USA5A), filed on the same date herewith. At one end of the ink cartridge bay 472 is an opening 476 through which the ink cartridge 400 is inserted and removed. The opening 476 preferably has a shape corresponding to a cross section of the ink cartridge 400 to facilitate the correct orientation. At the other end is a cartridge interface assembly 478 for fluidly coupling the ink cartridge 400 with a liquid replenishment system in the imaging device 481. Various liquid replenishment systems are disclosed in commonly assigned patent application entitled Liquid Ink Replenishment System for a Liquid Electrographic Imaging Device (Attorney Docket No. 53743USA7A), filed on the same date herewith.

The cartridge interface assembly 478 includes a shroud 483 for receiving cap 440. First assembly portions 428, 430, 432 (see FIG. 7) on the removable ink cartridge 400 are adapted to engage with second assembly portions 484, 486 and 488, respectively. Each of the first and second assembly portions are self sealing so as to prevent leakage from the ink cartridge 400 or the imaging device when the cartridge 400 is removed. In the illustrated embodiment, the first assembly portions 428, 430, 432 are integrally formed with the removable ink cartridge 400 and the second assembly portions 484, 486, 488 are integrally formed with a bulkhead 485 on the electrographic imaging device.

Drive magnet 490 is coupled to the actuator 180 by shaft 492 and is positioned to magnetically couple with impeller magnet 494 to drive impeller 426. The impeller magnet 494 is preferably contained within the outer shell 402 to minimize leakage of ink. The drive magnet 490 preferably has a shape complementary to the shape of the impeller magnet 494. The magnetic coupling between the magnets 490, 494 is sufficient to transfer rotational energy to the impeller 426, but is easily decoupled when the ink cartridge 400 is removed from the imaging device.

The ink cartridge 400 has a longitudinal axis 480 that corresponds with the longitudinal axis 482 on the cartridge interface assembly 478. As the ink cartridge 400 is advanced along longitudinal axis 480, the cap 440 is received by the shroud 483 and the magnets 490, 494 couple. Latch 495 optionally engages with edge 496 of the cartridge 400 to retain the cartridge in the ink cartridge bay 472. Detector 498 is optionally mounted in the ink cartridge bay 472 in a position to engage with the color key tab 414.

Figure 7:
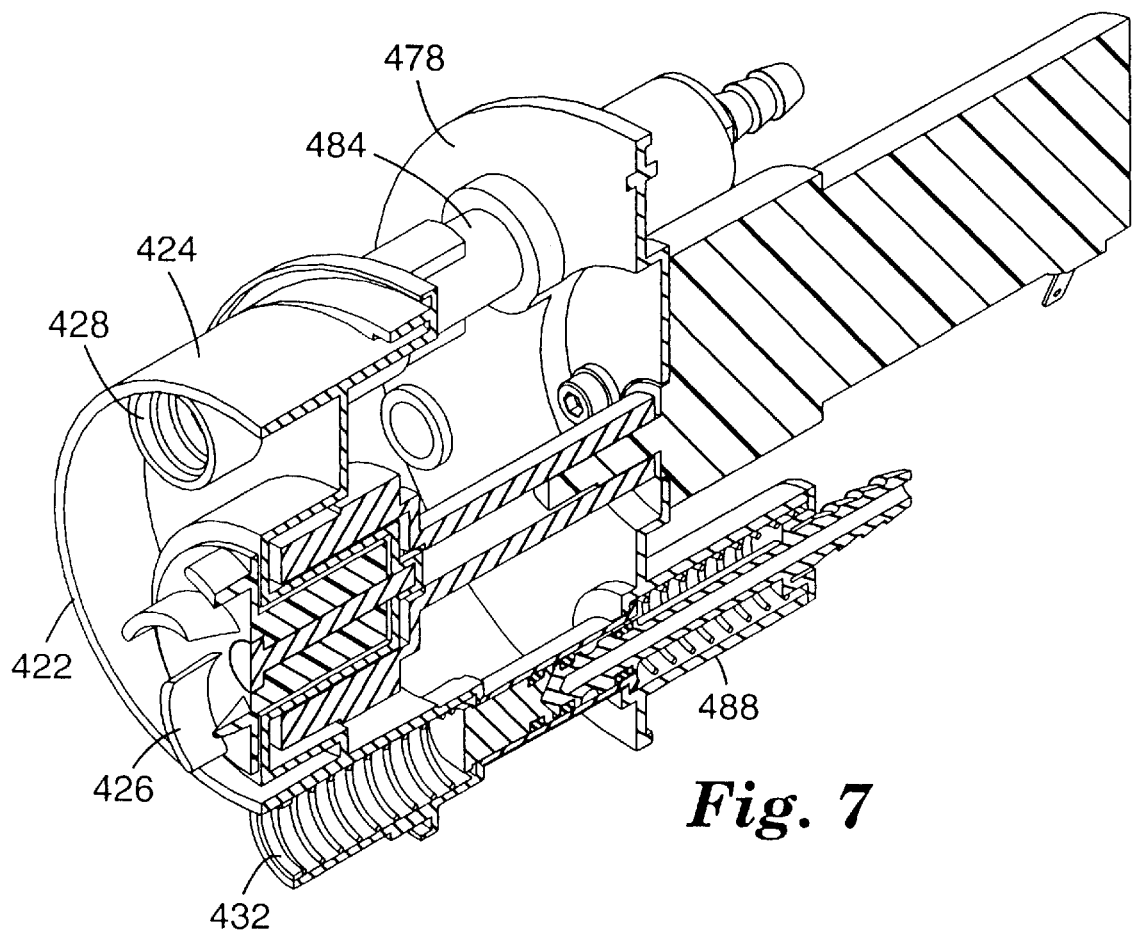
FIG. 7 is a side sectional view of a cartridge assembly interface utilizing a valve assembly in accordance with the present invention.

FIG. 7 is a perspective view of the cartridge interface assembly 478 fully engaged with the disk seal assembly 424. The first assembly portions 428, 430 (see FIG. 6), 432 and second assembly portions 484, 486 (see FIG. 6), 488 are open when the ink cartridge 400 is fully engaged with the cartridge interface assembly 478. The rear view of the disk seal assembly 424 illustrates the flange 422 for receiving an internal container, such as a collapsible bag (not shown) surrounding the impeller 426. The first assembly portion 428 is fluidly coupled to the container surrounding the flange 422. The first assembly portion 432 is positioned to fluidly couple with the region between the outer shell 402 and the internal container.

All patent and patent applications, including those disclosed in the background of the invention, are hereby incorporated by reference. The present invention has now been described with reference to several embodiments thereof. It will be apparent to those skilled in the art that many changes can be made in the embodiments described without departing from the scope of the invention. Thus, the scope of the present invention should not be limited to the structures described herein, but rather by the structures described by the language of the claims, and the equivalents of those structures.

We claim:

1. A valve assembly for fluidly coupling a removable ink cartridge to an imaging device, comprising:
    a first assembly portion comprising a first housing having first valve portion biased to a closed position, the first valve portion having a first interface surface at a distal end;
    a second assembly portion comprising a second housing having a second valve portion biased to a closed position, the second valve portion having a second interface surface at a distal end adapted to engage with the first interface surface at a valve interface; and
    a forward seal adapted to engage with the first interface surface and the second interface surface to prevent fluid from collecting at the valve interface when the first and second valve portions are in the closed position, whereby the valve interface is formed immediately upon engagement of the first and second assembly portions.

2. The valve assembly of claim 1 wherein the forward seal is located on the second valve portion.

3. The valve assembly of claim 1 wherein the forward seal is engaged with the first interface surface and the second interface surface at the valve interface when the first and second valve portions are in an open position.

4. The valve assembly of claim 1 wherein the forward seal is engaged with the first interface surface and the second interface surface at the valve interface until disengagement of the first and second valve portions.

5. The valve assembly of claim 1 further comprising a raised portion extending around a perimeter of the first interface surface adapted to engage with the forward seal.

6. The valve assembly of claim 1 wherein the first interface surface comprises a shape generally complementary to a shape of the second interface surface.

7. The valve assembly of claim 1 wherein the first interface surface is self-centering when engaged with the second interface surface.

8. The valve assembly of claim 1 wherein the valve interface centers the first valve portion relative to the second valve portion.

9. The valve assembly of claim 1 wherein the first and second interface surfaces comprise generally conical shapes.

10. The valve assembly of claim 1 wherein at least one of the interface surfaces comprises an elastomeric material.

11. The valve assembly of claim 1 wherein the forward seal is integrally formed with one of the valve portions.

12. The valve assembly of claim 1 wherein at least one of the valve portions comprises an elastomeric material.

13. The valve assembly of claim 1 wherein the forward seal is located at a distal end of the second valve portion, the second assembly portion comprising:
 a fluid channel in the second valve portion behind the forward seal;
 a rear seal behind the fluid channel; and
 a sleeve biased to engage with the forward seal and the rear seal when the second assembly portion is in the closed position.

14. The valve assembly of claim 13 wherein the first housing biases the sleeve into the second housing when the valve assembly is in an engaged configuration.

15. An ink cartridge including one of the assembly portions of the valve assembly of claim 1.

16. A valve assembly for fluidly coupling a removable ink cartridge to an imaging device, comprising:
 a first assembly portion comprising a first housing having first valve portion biased to a closed position, the first valve portion having a first interface surface at a distal end;
 a second assembly portion comprising a second housing having a second valve portion biased to a closed position, the second valve portion having a second interface surface at a distal end adapted to engage with the first interface surface at a valve interface; and
 a raised portion extending around a perimeter of the first interface surface adapted to engage with the second interface surface to prevent fluid from collecting at the valve interface when the first and second valve portions are in the closed position, whereby the valve interface is formed immediately upon engagement of the first and second assembly portions.

17. An ink cartridge for an electrographic imaging device, the electrographic imaging device having a first valve portion with a first interface surface at a distal end, the ink cartridge comprising:
 an ink cartridge housing;
 a second assembly portion comprising a second housing having a second valve portion biased to a closed position, the second valve portion having a second interface surface at a distal end adapted for self-centering engagement with the first interface surface at a fluid tight valve interface; and
 a forward seal adapted to engage with the first interface surface and the second interface surface to prevent fluid from collecting at the valve interface when the first and second valve portions are in the closed position, whereby the valve interface is formed immediately upon engagement of the first and second assembly portions.

18. The ink cartridge of claim 17 wherein the forward seal is located on the second valve portion.

19. The ink cartridge of claim 17 wherein the second assembly portion is formed integrally with a portion of the ink cartridge.

20. A method of fluidly coupling a removable ink cartridge to an imaging device, comprising the steps of:
 biasing a first valve portion of a first assembly portion in a valve assembly to a closed position, the first valve portion having a first interface surface at a distal end;
 biasing a second valve portion of a second assembly portion in the valve assembly to a closed position, the second valve portion having a second interface surface at a distal end adapted to engage with the first interface surface at a valve interface;
 positioning a forward seal adapted to engage with the first interface surface and the second interface surface at the valve interface when the first and second valve portions are in the closed position;
 locating a raised portion extending around a perimeter of the first interface surface adapted to engage with the forward seal:
 advancing the first and second valve portions to an open position while maintaining the valve interface in a substantially fluid tight configuration; and
 disengaging the valve assembly while maintaining the valve interface in a substantially fluid tight configuration.

21. The method of claim 20 comprising centering the first valve portion with respect to the second valve portion.

22. The method of claim 20 wherein the step of engaging the valve assembly comprises the step of disengaging a sleeve extending across the forward seal, a fluid channel, and a rear seal on the second assembly portion.

* * * * *